United States Patent [19]

Swanson et al.

[11] Patent Number: 4,532,368

[45] Date of Patent: Jul. 30, 1985

[54] PROCESS FOR MAKING META- AND PARA-ALKYLPHENOLS

[75] Inventors: Barry J. Swanson; Ronald L. Shubkin, both of Baton Rouge, La.

[73] Assignee: Ethyl Corporation, Richmond, Va.

[21] Appl. No.: 575,757

[22] Filed: Feb. 1, 1984

[51] Int. Cl.³ .............................................. C07C 37/11
[52] U.S. Cl. .................... 568/791; 568/804; 568/794
[58] Field of Search ........................ 568/791, 794, 804

[56] References Cited

U.S. PATENT DOCUMENTS

| 3,706,807 | 12/1972 | Etherington | 568/791 |
| 3,728,408 | 4/1973 | Tobias | 568/791 |
| 3,992,455 | 11/1976 | Leston | 568/791 |
| 4,283,573 | 8/1981 | Young | 568/791 |
| 4,371,714 | 2/1983 | Young | 568/791 |
| 4,391,998 | 7/1983 | Wu | 568/791 |

FOREIGN PATENT DOCUMENTS

| 0043943 | 11/1974 | Japan | 568/804 |
| 1150209 | 4/1969 | United Kingdom | 568/791 |
| 352868 | 10/1972 | U.S.S.R. | 568/791 |
| 455743 | 2/1975 | U.S.S.R. | 568/794 |
| 692825 | 10/1979 | U.S.S.R. | 568/791 |
| 730675 | 4/1980 | U.S.S.R. | 568/794 |
| 863588 | 11/1981 | U.S.S.R. | 568/804 |

OTHER PUBLICATIONS

Venuto et al., "Journal of Catalysis", vol. 4, (1966), pp. 81–98.

Primary Examiner—Werren B. Lone
Attorney, Agent, or Firm—Donald L. Johnson; John F. Sieberth; Joseph D. Odenweller

[57] ABSTRACT

A process for making a mixture of meta- and para-alkylphenols by contacting a mixture of phenol, ortho-alkylphenol and an alkylating agent (e.g. olefins or lower alcohols) with a zeolite having a silica:alumina ratio of at least 12:1 under alkylating conditions to obtain a mixture of ortho-, meta- and para-alkylphenols and then separating at least part of the ortho-alkylphenol which is recycled to a subsequent alkylation process carried out in the same manner.

20 Claims, No Drawings

PROCESS FOR MAKING META- AND PARA-ALKYLPHENOLS

BACKGROUND OF THE INVENTION

Alkylated phenols find many uses in industry. They are valuable starting materials for making many antioxidants. In some areas ortho-alkylphenols are the desired isomer. In other areas, para-alkylphenols or mixtures of para- and meta-alkylphenols are more desirable. For example, mixtures of meta- and para-alkylphenols can be reacted with phosphorus oxychloride to form triaryl phosphates which are useful gasoline additives.

Ortho-alkylphenols can be made following the process described in U.S. Pat. No. 2,831,898. When making other alkyl phenol isomers, phenol is usually alkylated using an acidic catalyst which forms mixtures of ortho-, meta- and para-alkylphenols. A useful process for making mixtures of isopropyl phenols which are high in para-isopropylphenols is described in U.S. Pat. No. 4,391,998. According to that patent, a mixture of phenol and either isopropanol or propylene is contacted with a crystalline zeolite catalyst to form a mixture of ortho-, meta- and para-isopropylphenol having an increased para-isopropylphenol content but still containing substantial amounts of ortho-alkylphenol.

SUMMARY OF THE INVENTION

It has now been discovered that a mixture consisting mainly of meta- and para-alkylphenols can be efficiently and economically obtained by contacting a mixture of ortho-alkylphenol, phenol and either olefin or alcohol with a crystalline zeolite catalyst under alkylation conditions to obtain a mixture of ortho-, meta- and para-alkylphenols. Ortho-alkylphenol is distilled from this mixture and recycled to a subsequent alkylation carried out in the same manner wherein the recovered ortho-alkylphenol forms part of the feed stock. Surprisingly it has been found that recycling the ortho-alkylphenol does not substantially increase the ratio of ortho- to meta- and para-alkylphenol in the alkylated product, relative to the product obtained when phenol alone is used in the feed.

DESCRIPTION OF PREFERRED EMBODIMENTS

A preferred embodiment of the invention is a process for making a mixture of meta- and para-alkylphenols containing only minor amounts of ortho-alkylphenol, said process comprising (a) passing a mixture of phenol, ortho-alkylphenol, and an alkylating agent selected from the group consisting of lower alcohols and olefins, through a zeolite catalyst having a silica:alumina mole ratio of at least 12:1 under alkylating conditions at a temperature of about 200°–500° C. to obtain a mixture of ortho, meta- and para-alkylphenols, (b) separating at least part of said ortho-alkylphenols from said mixture of ortho-, meta- and para-alkylphenols forming said mixture of meta- and para-alkylphenols containing only minor amounts of ortho-alkylphenols and (c) recycling the separated ortho-alkylphenol to a subsequent alkylation carried out as defined in step (a), (b) and (c) wherein said separated ortho-alkylphenol is used as said ortho-alkylphenol in said mixture of phenol, ortho-alkylphenol and alkylating agent in step (a).

The crystalline zeolite used in the present process are members of a class of zeolitic materials which exhibit unusual properties. These zeolites have unusually low alumina contents, i.e. high silica to alumina mole ratios. Even with this low alumina content, they have been found to be very active catalyst. These zeolites retain their crystallinity for long periods in spite of the presence of steam at high temperature which induces irreversible collapse of the framework of other zeolites, e.g. the X and A type zeolites.

An important characteristic of the crystal structure of the zeolites used in the present process is that they provide a selective constrained access to and egress from the intracrystalline free space by virtue of having an effective pore size which is intermediate between the small pore size of Linde A molecular sieve and the large pore size of Linde X molecular sieve. The pore windows of the zeolites are about the size that would be provided by a 10-membered ring of silicon atoms connected through oxygen atoms.

These rings are those formed by the regular disposition of the tetrahedra making up the anionic framework of the crystalline zeolite. The oxygen atoms being bonded to the silicon (or aluminum, etc.) atoms at the center of the tetrahedra.

The silica to alumina mole ratio referred to may be determined by conventional analysis. This ratio is meant to represent the ratio in the rigid anionic framework of the zeolite crystal and to exclude aluminum in the binder or in cationic or other forms within the channels. Although zeolite with silica to alumina mole ratios of at least 12 are useful, it is preferred to use zeolite having substantially higher silica:alumina ratios, e.g. 1600:1 and above. In addition, zeolite otherwise characterized herein but which are substantially free of aluminum are useful in the present process.

The zeolite as defined herein are described as the pentasil family of zeolites and are exemplified by ZSM-5, ZSM-11, ZSM-12, ZSM-23, ZSM-35, ZSM-38, ZSM-48, Silicalite and Silicalite-2. ZSM-5 is described in U.S. Pat. No. 3,702,886. ZSM-11 is described in U.S. Pat. No. 3,709,979. ZSM-12 is described in U.S. Pat. No. 3,832,449. ZSM-23 is described in U.S. Pat. No. 4,076,842. ZSM-35 is described in U.S. Pat. No. 4,016,245. ZSM-38 is described in U.S. Pat. No. 4,046,859. ZSM-48 is described in published European Patent Application No. 80 300,463. The entire contents of each of the foregoing references is incorporated herein for their disclosure of the crystalline zeolite catalyst used to conduct the present process.

Silicalite is described in "Silicalite, A New Hydrophobic Crystalline Silica Molecular Sieve", Flannigan, et al., Nature, Vol. 271, Feb. 9, 1978, pages 512–516. Silicalite-2 is described in "Silicalite-2, A Silica Analouge of the Alumina Silicate Zeolite ZSM-11", Bibby, et al., Nature, Vol. 280, Aug. 23, 1979, pages 664–665. The foregoing citations from Nature are also incorporated herein by reference for their disclosure of Silicalite and Silicalite-2. The incorporation of the above-identified patents and references should not be construed as limiting the crystalline zeolite to those having the specific silica:alumina mole ratio discussed therein, it now being known that such zeolite may be substantially aluminum-free and yet have the same crystal structure as the disclosed materials.

The zeolites described herein are almost catalytically inactive when first prepared but can be activated by heating in an inert atmosphere at about 540° C. for one hour followed by base exchange with an ammonium salt followed by calcination at 540° C. in air or from fifteen minutes to about twenty-four hours.

The preferred crystalline zeolites used in the present process are ZSM-5, ZSM-11, Silicalite and Silicalite-2. ZSM-5 and Silicalite are the most preferred catalyst.

When made in the alkali metal form, the zeolite is conveniently converted to the hydrogen form by intermediate formation of the ammonium form as a result of ammonium ions exchange and calcination of the ammonium form to yield the hydrogen form. In addition to the hydrogen form, other forms of zeolite wherein the original alkali metal has been reduced to less than about 1.5% by weight may be used. Thus, the original alkali metal of the zeolite may be replaced by ion exchange with other suitable metal cations of Group I–VIII of the Periodic Table, including by way of example, nickel, copper, zinc, paladium, calcium or rare earth metals.

In practicing a particularly desired chemical conversion, it may be useful to incorporate the above-described crystalline zeolite with a matrix comprising another material resistant to the temperature and other conditions employed in the process. Such matrix material is useful as a binder and imparts greater resistance to the catalyst for the severe temperature, pressure and reactant feed stream velocity conditions encountered in the process.

Useful matrix material includes both synthetic and naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kalolin families, which families include the sub-bentonites and the kaloline commonly known as Dixie, McNamee-Georgia and Florida clays or others in which the main mineral constituent is haloysite, kaolinite, dickite, nacrite or anauxite. Such clays can be used in the raw state as originally mined or initially subjected to calcination, acid treatment or chemical modification.

The crystalline zeolites used in the present process may be modified prior to use by combining with small amounts of a promoter, generally in the range of about 0.5–40 weight percent. Possible promoters include but are not limited to boron oxide, antimony oxide, calcium oxide, calcium carbonate, magnesium oxide, amorphous silica and phosphorus oxide. Modification of the zeolite with the desired oxide or oxides can readily be effected by contacting the zeolite with a solution of an appropriate compound of the element to be introduced followed by drying and calcining to convert the compound to its oxide form.

Representative phosphorus-containing compounds which may be used include derivatives of groups represented by $PX_3$, $RPX_2$, $R_2PX$, $R_3P$, $X_3PO$, $(XO)_3PO$, $(XO)_3P$, $R_3P=O$, $R_3P=S$, $RPO_2$, $RPS_2$, $RP(O)(OX)_2$, $RP(S)(SX)_2$, $R_2P(O)OX$, $R_2F(S)SX$, $RP(OX)_2$, $RP(SX)_2$, $ROP(OX)_2$, $RSP(SX)_2$, $(RS)_2PSP(SR)_2$, and $(RO)_2POP(OR)_2$, wherein R is an alkyl or aryl, such as a phenyl radical and X is hydrogen; R, or halide. These compounds include primary, $RPH_2$, secondary, $R_2PH$ and tertiary, $R_3P$, phosphines such as butyl phosphine; the tertiary phosphine oxides $R_3PO$, such as tributylphosphine oxide, the tertiary phosphine sulfides, $R_3PS$, the primary $RP(O)(OX)_2$, and secondary, $R_2P(O)OX$, phosphonic acids such as benzene phosphonic acid; the corresponding sulfur derivatives such as $RP(S)(SX)_2$ and $R_2P(S)SX$, the esters of the phosphonic acids such as alkyl phosphonate, $(RO)_2P(O)H$, dialkyl alkyl phosphonates, $(RO)_2P(O)R$, and alkyl dialkylphosphonates, $(RO)P(O)R_2$; phosphinous acids, $R_2POX$, such as diethylphosphinous acid, primary $(RO)P(OX)_2$, secondary, $(RO)_2POX$, and tertiary $(RO)_3P$, phosphites and esters thereof such as the monopropyl ester, alkyl dialkylphosphinites, $(RO)PR_2$, and dialkyl alkylphosphinite, $(RO)_2PR$, esters. Corresponding sulfur derivatives may also be employed including $(RS)_2P(S)H$, $(RS)_2P(S)R$, $(RS)P(S)R_2$, $R_2PSX$, $(RS)P(SX)_2$, $(RS)_2PSX$, $(RS)_3P$, $(RS)PR_2$ and $(RS)_2PR$. Examples of phosphite esters include trimethylphosphite, triethylphosphite, diisopropylphosphite, butylphosphite, and pyrophosphites such as tetraethylpyrophosphite. The alkyl groups in the mentioned compounds preferably contain one or four carbon atoms.

Other suitable phosphorus-containing compounds include the phosphorus halides such as phosphorus trichloride, bromide, and iodide, alkyl phosphorodichloridites, $(RO)PCl_2$, dialkyl phosphorochloridites, $(RO)_2PCl$, dialkylphosphinochloridites, $R_2PCl$, alkyl alkylphosphonochloridates, $(RO)(R)P(O)Cl$, dialkyl phosphinochloridates, $R_2P(O)Cl$ and $RP(O)Cl_2$. Applicable corresponding sulfur derivatives include $(RS)PCl_2$, $(RS)_2PCl$, $(RS)(R)P(S)Cl$ and $R_2P(S)Cl$.

Preferred phosphorus-containing compounds include diphenyl phosphine chloride, trimethylphosphite, phosphorus trichloride, phosphoric acid, phenyl phosphine oxychloride, trimethylphosphate, diphenyl phosphinous acid, diphenyl phosphinic acid, diethylchlorothiophosphate, methyl acid phosphate and other alcohol-$P_2O_5$ reaction products.

Particularly preferred are ammonium phosphates, including ammonium hydrogen phosphate, $(NH_4)_2HPO_4$, and ammonium dihydrogen phosphate, $NH_4H_2PO_4$.

Reaction of the zeolite with the phosphorus compound is effected by contacting the zeolite with such compound. Where the treating phosphorus compound is a liquid or a solid, such compound can be in solution in a solvent at the time contact with the zeolite is effected. Any solvent relatively inert with respect to the treating compound and the zeolite may be employed. Suitable solvents include water and aliphatic, aromatic or alcoholic liquids. Where the phosphorus-containing compound is, for example, trimethylphosphite or liquid phosphorus trichloride, a hydrocarbon solvent such as octane may be employed. The phosphorus-containing compound may be used without a solvent, i.e., as a neat liquid. Where the phosphorus-containing compound is in the gaseous phase, such as where gaseous phosphorus trichloride is employed, the treating compound can be used by itself or can be used in admixture with a gaseous diluent relatively inert to the phosphorus-containing compound and the zeolite, such as air or nitrogen, or with an organic solvent, such as octane or toluene.

Prior to reacting the zeolite with the phosphorus-containing compound, the zeolite may be dried. Drying can be effected in the presence of air and elevated temperatures may be employed. However, the temperature should not be such that the crystal structure of the zeolite is destroyed.

Heating of the phosphorus-containing catalyst subsequent to preparation and prior to use is also preferred. The heating can be carried out in the presence of oxygen—for example, in air. Heating can be at a temperature of about 150° C. However, higher temperatures, e.g., up to about 500° C., are preferred. Heating is generally carried out for 3–5 hours but may be extended to 24 hours or longer. While temperatures above about 500° C. can be employed, they are generally not necessary.

The amount of phosphorus incorporated with the zeolite should be at least about 0.25 percent by weight. However, it is preferred that the amount of phosphorus be at least about 1 percent by weight when the zeolite is combined with a binder, e.g. 35 weight percent of alumina. The amount of phosphorus can be as high as about 25 percent by weight or more depending on the amount and type of binder present. Preferably, the amount of added to the zeolite will be between about 0.5 and about 15 percent by weight of the phosphorus-modified zeolite composition.

Amorphous silica promoter is applied to the zeolite by contacting with silanes and silicones. Acid catalyst to enhance the silation process can also be employed. Examples include trifluoroacetic acid and para-toluene sulfonic acid.

The silanes have the general formula:

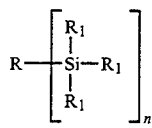

wherein n is 1 or 2; R is a reactive group such as hydrogen, alkoxy, halogen, carboxy, amino, and acetamide; $R_1$ can be the same as R, or $R_1$ can be alkyl of 1 to about 40 carbon atoms, an alkyl or aryl carboxylic acid wherein the alkyl group contains about 1 to 30 carbon atoms and the aryl group contains about 6 to 24 carbon atoms; an aryl of about 6 to 24 carbons which may be further substituted; or an alkaryl or aralkyl containing about 7 to 30 carbon atoms. Preferably, the alkyl group of an alkyl silane has from 1 to 4 carbon atoms and the carbon chain of an alkoxy group has from 1 to 6 carbon atoms. Alkoxy-containing silanes are preferred. One such preferred alkoxy-containing silane is tetraethoxysilane (ethylorthosilicate). Mixtures of the above compounds can also be used.

The silicone compounds have the general formula:

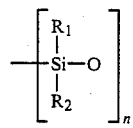

wherein $R_1$ is hydrogen, fluorine, hydroxy, alkyl, aralkyl, alkaryl or fluoro-alkyl. The hydrocarbon substituents generally contain from 1 to 10 carbon atoms and preferably are methyl or ethyl groups. $R_2$ is selected from the same group as $R_1$, other than hydrogen, and n is an integer of at least 10 and generally in the range of 10 to 1000. The molecular weight of the silicone compound employed is generally between about 500 to 20,000 and preferably within the approximate range of 1000 to 10,000. Representative silicone compounds include dimethylsilicone, diethylsilicone, phenylmethylsilicone, methylhydrogensilicone, ethylhydrogensilicone, phenylhydrogensilicone, methylethylsilicone, phenylethylsilicone, diphenylsilicone, methyltrifluoropropylsilicone, ethyltrifluoropropylsilicone, polydimethylsilicone, tetrachlorophenylmethylsilicone, tetrachlorophenylethylsilicone, tetrachlorophenylhydrogensilicone, tetrachlorophenylphenylsilicone, methylvinylsilicone and ethylvinylsilicone. Phenylmethylsilicone is preferred.

The promoter can be in the form of a liquid, gas or solid. A solvent can be employed to dissolve the promoter, followed by contact with the crystalline silica. Any solvent which is inert to reaction with the promoter can be used, including water, alcohols, and aliphatic or aromatic hydrocarbons. The promoter can also be used neat, by soaking or admixture with the crystalline silica or by gaseous deposition.

The promoter oxides or precursors, used neat or dissolved in a suitable solvent such as n-hexane, benzene, toluene, xylene, chloroform or carbon tetrachloride, are contacted with the activated crystalline silica between 25° C. and 100° C. for a period of time sufficient to deposit the desired amount of promoter thereon. The contact time will usually vary from 1 to 16 hours. Solvent, if used, is then removed by filtration or evaporation. The promoted crystalline silica is then dried at 95° to 125° C. in nitrogen or air for several hours. Activation of promoted crystalline silica is achieved by calcination at temperatures up to about 600° C. Preferably, the calcination temperature is raised slowly, e.g., 1° to 10° C./min. until about 600° C. is reached and then held for a time sufficient to complete the activation.

The preferred method for adding amorphous silica as promoter to the zeolite catalyst, is contacting the zeolite and tetraethyl-orthosilicate in hexane, removing the solvent and calcining.

The reaction process may be carried out as a batch type, semi-continuous or continuous operation utilizing a fixed or moving bed catalyst system. The catalyst, after use in a moving bed reactor, is conducted to a regeneration zone wherein excess coke is burned from the catalyst in an oxygen-containing atmosphere (e.g. air) at an elevated temperature, after which the regenerated catalyst is recycled to the conversion zone for further contact with the charge stock. In a fixed bed reactor, regeneration is carried out in a conventional manner where an inert gas containing a small amount of oxygen (0.5–2%) is used to control burning of the coke so as to limit the temperature to a maximum of around 500° C.–550° C.

The reaction conditions for carrying out the process of this invention will, of course, vary with the specific reactants employed and the nature of the equipment (batch type, fixed bed, FCC, etc.). Generally speaking, the temperature should be between about 100° C. and 600° C., preferably between 200° C. and 500° C. The pressure may be between $10^4$ Pa (0.1 atm) and $10^7$ Pa (100 atm), but operating pressures within the range of $10^5$ Pa to $2 \times 10^6$ Pa are preferred.

The alkylating agent can be either an alcohol or an olefin. For example, the alkylating agent can be methanol, ethanol, propanol, isopropanol, butanol, isobutanol, tert-butanol, pentanol, isopentanol, hexanol, sec-hexanol, 2-ethylhexanol, 1-methylhexanol, 1-ethylhexanol, 1-propylhexanol, decanol, 2-ethyloctanol, 1-methyldecanol, dodecanol, 1-methyldodecanol, octadecanol, eicosanol, docosanol, tetracosanol, hexacosanol, triacontanol, ethylene, propylene, butene, isobutene, 1-pentene, 2-pentene, isopentene, 1-hexene, 2-hexene, 3-methyl-1-hexene, 2-ethyl-1-hexene, octent, 2-octene, 1-decene, 2-decene, 3-decene, 2-ethyl-1-dodecene, 4-dodecene, 1-eicosene, 1-docoene, 2-docoene, 1-triacontene and the like.

The preferred alkylating agents are the alcohols. The preferred alcohols are the alcohols containing from 1 to about 12 carbon atoms. The more preferred alcohols are the lower alcohols containing from 2 to about 4 carbon atoms such as ethanol, 1-propanol, 2-propanol, 1-butanol, 2-butanol, isobu- tanol, tertbutanol and the like. The most preferred alkylating agent is ethanol.

The feed material to the process is a mixture of phenol and an ortho-alkyphenol. The mixture can contain about 5–95 weight percent phenol and 5–95 weight percent ortho-alkylphenol. Other phenol isomers and inert diluents can be included in the feed stream. The ortho-alkylphenol used in the feed stream is that which is a by-product from a pevious alkylation carried out in the same manner. Thus the chemical identity of the ortho-alkylphenol used in the feed mixture is determined by the alkylating agent used in the process series. For example, if ethanol is being used as the alkylating agent, then the ortho-alkylphenol used in the feed stream will be ortho-ethylphenol. Likewise, if isopropanol or propylene is used as the alkylating agent, then the orthoalkyl phenol co-feed will be ortho-isopropylphenol. The amount of alkylating agent fed with the phenol mixture should be an amount which provides the required amount of alkyl groups. A useful range is about 0.5–10 moles of alkylating agent per mole of phenol and ortho-alkylphenol in the phenolic feed stream. A more preferred amount of alkylating agent is about 0.75–1.75 moles of alkylating agent per moles of phenol and ortho-alkylphenol in the feed stream. A most preferred amount of alkylating agents is about 0.9–1.25 moles of alkylating agent per mole of phenol in the phenolic feed stream.

The process is readily carried out by passing the phenolic mixture and the alkylating agent through a catalyst bed at the proper temperature. A useful temperature range is about 100°–600° C. A more preferred temperature range is about 200°–500° C. The pressure does not appear to be critical. A useful pressure range is from about 0.01–100 atmosphere ($10^4$Pa–$10^7$Pa). In a preferred embodiment the pressure is about 1–20 atmospheres ($10^5$–$10^6$ Pa).

The process may be conducted in the liquid phase or in the vapor phase depending upon the temperature-pressure condition. Preferably, the process is conducted such that the alkylating agent and the phenolic mixture is substantially in the vapor phase although some liquid components may be present.

Other potential alkylating agents for use with the process include ethers (e.g. diethyl ether, methylethyl ether, dipropyl ether, and the like), alkyl halides (e.g. ethyl chloride, ethyl bromide, isopropyl chloride, normal propyl bromide, normal butyl chloride, 2-bromobutane, and the like).

The process can be carried out on a continuous basis by placing the catalyst in a tubular catalyst column, heating the catalyst to the proper temperature and passing the mixture of phenol, orthoalkyl phenol and alkylating agents through the heated catalyst column.

The contact time of the reactants with the catalyst bed under alkylating conditions can range from about one minute or less to eight hours or more. A preferred contact time is from about 3 minutes up to 1 hour.

The following examples show the preparation of several of the modified zeolite catalyst and also show the method of conducting the process and the benefits achieved thereby.

EXAMPLE 1

Preparation of Phosphorus-Modified Zeolite

Eight grams of diammonium hydrogen phosphate was dissolved in 30 ml of water. Then 20 grams of ammonium exchanged ZSM-5 zeolite was added to the aqueous solution and the mixture heated to 80° C. and held at that temperature for 2 hours. The mixture was then filtered and the solid catalyst then air dried and calcined at 500° C. for 12 hours.

EXAMPLE 2

Preparation of Silicon-Modified Zeolite

In a flask was placed 100 mL of hexane and 1.5 grams of tetraethylorthosilicate. To this hexane solution was added 8.5 grams of Silicalite and the mixture stirred at ambient temperature for one hour. The solvent was removed and the catalyst recovered and air dried at 95° C. in a stream of nitrogen. The catalyst was then calcined at gradually increasing temperatures from 120° to 500° C. over a 12 hour period.

EXAMPLES 3–7

A series of alkylations was conducted by placing approximately 2.0 grams of phosphorus-modified ZSM-5 in a stainless steel reaction tube, and passing phenol or a mixture of phenol with various amounts of ortho-ethylphenol through the tube at 450° C. The alkylating agent included with the phenolic mixture was ethanol in amount equal to 1 mole of ethanol per mole of phenol in the phenolic mixture. The first run in the series was conducted using phenol without any ortho-ethylphenol in the feed stream. This can be considered the base line for comparison with subsequent runs using various amounts or orthoethylphenol (OEP). The following table shows the weight percent of ethyl phenol (EP) in the initial product stream and also the ortho:meta:para ratio. The table then shows the weight percent of ethyl phenols in the product stream after subtracting the amount of ortho-ethylphenol that would be needed to provide the concentration of ortho-ethylphenol in the initial feed stream. Finally, the table shows the resultant ortho-meta:para ratio after distillation to remove the ortho-ethylphenol for recycle.

TABLE

|  | Example | | | | |
| --- | --- | --- | --- | --- | --- |
|  | 3 | 4 | 5 | 6 | 7 |
| wt % OEP in 1:1 phenol/ethanol feed | 0 | 1 | 2 | 4 | 6 |
| wt % EPs in Initial Product | 13.6 | 16.8 | 16.7 | 21.5 | 22.1 |
| Initial Composition of EPs | | | | | |
| wt % ortho | 26 | 28 | 31 | 31 | 32 |
| wt % meta | 47 | 48 | 45 | 47 | 47 |
| wt % para | 27 | 24 | 24 | 22 | 21 |
| wt % EP in Product after Distilling Out OEP for Recycle | 13.6 | 15.8 | 14.7 | 17.5 | 16.1 |
| Final Composition of EPs | | | | | |
| wt % ortho | 26 | 24 | 21 | 14 | 7 |
| wt % meta | 47 | 51 | 52 | 57 | 64 |
| wt % para | 27 | 25 | 27 | 29 | 29 |

As the above results demonstrate, the addition of ortho-ethylphenol to the phenolic feed stream causes an increase in the amount of ortho-ethylphenols in the product. The initial composition of the product shows a slight steady increase in ortho-ethylphenol and decrease in para-ethylphenol as the amount of ortho-ethylphenol in the feed is increased. However, when adjusted for the amount of ortho-ethylphenol that is distilled out to provide the amount required as recycle in the phenolic feed, it can be seen that the final product composition drops from 26 weight percent ortho-ethylphenol to only 7 weight percent ortho-ethylphenol as the amount of ortho-ethylphenol in the feed increases from 0 to 6 weight percent. The resultant ethylphenol mixture after distilling out unreacted phenol and ortho-ethyl-phenol required for recycle consists of 93 weight percent meta- and para-phenols. An even greater amount of meta- and para-phenol composition could be obtained by further increasing the amount of ortho-ethylphenol distilled from the initial product composition and used for recycle. Furthermore, the yield after distilling out OEP is greater than when the reaction is carried out without recycle.

Although in the most preferred embodiment the feed to the alkylation reaction includes both phenol and o-alkylphenol in addition to alkylating agent, the initial reaction in a series need not include the o-alkylphenol. In the initial reaction the inclusion of o-alkylphenol is optional. In the next run o-alkylphenol can be included since it can be obtained by distillation from the resultant mixture of ortho-, meta- and para- alkylphenols obtained in a previous run.

The beneficial effect of including o-alkylphenol with the phenol and alkylating agent contacted with the crystalline zeolite can be obtained without the necessity of recycling o-alkylphenol. In other words the increase in the amount of meta- and para- alkylphenols can be achieved by merely contacting a mixture of phenol, o-alkylphenol and alkylating agent with the crystalline zeolite catalyst under alkylating conditions whether or not the o-alkylphenol is removed from the product for recycle.

We claim:

1. A process for making a mixture of meta- and para-alkylphenols containing only minor amounts of ortho-alkylphenol, said process comprising
    (a) passing a mixture of phenol, ortho-alkylphenol, and an alkylating agent selected from the group consisting of lower alcohols and olefins, through a zeolite catalyst having a silica:alumina mole ratio of at least about 12:1 under alkylating conditions at a temperature of about 200°–500° C. to obtain a mixture of ortho-, meta- and para-alkylphenols,
    (b) separating at least part of said ortho-alkylphenols from said mixture of ortho-, meta- and para-alkylphenols forming said mixture of meta- and para-alkylphenols containing only minor amounts of ortho-alkylphenols and
    (c) recycling the separated ortho-alkylphenol to a subsequent alkylation carried out as defined in step (a), (b) and (c) wherein said separated ortho-alkylphenol is used as said ortho-alkylphenol in said mixture of phenol, ortho-alkylphenol and alkylating agent in step (a).

2. A process of claim 1 wherein said zeolite catalyst is selected from the group consisting of ZSM-5, ZSM-11, ZSM-12, ZSM-23, ZSM-35, ZSM-38, ZSM-48, Silicalite and Silicalite-2.

3. A process of claim 2 wherein said zeolite catalyst is ZSM-5.

4. A process of claim 3 wherein said ZSM-5 is phosphorus promoted.

5. A process of claim 2 wherein said zeolite catalyst is Silicalite.

6. A process of claim 5 wherein said Silicalite is silicone promoted.

7. A process of claim 2 wherein said alkylating agent is an alcohol containing 1 to about 12 carbon atoms.

8. A process of claim 7 wherein said alcohol contains 2 to about 4 carbon atoms.

9. A process of claim 8 wherein said zeolite catalyst is ZSM-5.

10. A process of claim 9 wherein said ZSM-5 is phosphorus promoted.

11. A process of claim 8 wherein said zeolite catalyst is Silicalite.

12. A process of claim 11 wherein said Silicalite is silicone promoted.

13. A process of claim 1 wherein said alkylating agent is ethanol.

14. A process of claim 13 wherein said zeolite catalyst is ZSM-5.

15. A process of claim 14 wherein said ZSM-5 is phosphorus promoted.

16. A process of claim 13 wherein said zeolite catalyst is Silicalite.

17. A process of claim 16 wherein said Silicalite is silicon promoted.

18. A process for making a mixture of meta- and para-alkylphenols containing none or a minor amount of ortho-alkylphenol, said process comprising
    (a) contacting a mixture of phenol and alkylating agent selected from the group consisting of lower alcohols, olefins and mixtures thereof and optionally including an ortho-alkylphenol, with a crystalline zeolite catalyst having a silica: alumina mole ratio of at least 12:1 under alkylating conditions at a temperature of about 200°–500° C. to obtain a mixture of ortho-, meta- and para- alkylphenols,
    (b) separating at least part of said ortho-alkylphenol from said mixture of ortho-, meta- and para- alkylphenols forming said mixture of meta- and para-alkylphenols containing none or minor amounts of ortho-alkylphenol and
    (c) recycling the separated ortho-alkylphenol to a subsequent alkylation carried out to include the above steps (a) and (b) and optionally step (c).

19. A process of claim 18 further characterized in that said ortho-alkylphenol is included in step (a) and that at least part of said ortho-alkylphenol is recycled from step (b) of a previous process conducted according to claim 18.

20. A process for making a mixture of meta- and para-alkylphenols containing none or a minor amount of ortho-alkylphenol, said process comprising
    (a) contacting a mixture of phenol, an alkylating agent selected from the group consisting of lower alcohols, olefins and mixtures thereof and an ortho-alkylphenol with a crystalline zeolite catalyst having a silica:alumina mole ratio of at least 12:1 under alkylating conditions at a temperature of about 200°–500° C. to obtain a mixture of ortho-, meta- and para- alkylphenols and
    (b) separating at least part of said ortho-alkylphenol from said mixture of ortho-, meta- and para- alkylphenols forming said mixture of meta- and para-alkylphenols containing none or a minor amount of ortho-alkylphenol.

* * * * *